US012806314B2

(12) United States Patent
Conoci et al.

(10) Patent No.: US 12,806,314 B2
(45) Date of Patent: Nov. 24, 2026

(54) METHOD FOR THE ANTIBACTERIAL TREATMENT OF A SOLID SURFACE

(71) Applicant: INOVA BIOMEDICAL TECHNOLOGY S.R.L., Catania (IT)

(72) Inventors: Sabrina Conoci, Catania (IT); Francesco Traina, Catania (IT); Salvatore Petralia, Catania (IT)

(73) Assignee: INOVA BIOMEDICAL TECHNOLOGY S.R.L., Catania (IT)

( * ) Notice: Subject to any disclaimer, the term of this patent is extended or adjusted under 35 U.S.C. 154(b) by 449 days.

(21) Appl. No.: 18/266,092

(22) PCT Filed: Dec. 9, 2021

(86) PCT No.: PCT/IB2021/061504

§ 371 (c)(1),
(2) Date: Jun. 8, 2023

(87) PCT Pub. No.: WO2022/123483

PCT Pub. Date: Jun. 16, 2022

(65) Prior Publication Data

US 2024/0001003 A1 Jan. 4, 2024

(30) Foreign Application Priority Data

Dec. 9, 2020 (IT) ........................ 102020000030230

(51) Int. Cl.

*A61L 27/54* (2006.01)
*A61L 27/30* (2006.01)

(52) U.S. Cl.

CPC ............. *A61L 27/54* (2013.01); *A61L 27/306* (2013.01); *A61L 2300/102* (2013.01); *A61L 2300/404* (2013.01); *A61L 2420/02* (2013.01)

(58) Field of Classification Search

None
See application file for complete search history.

(56) References Cited

U.S. PATENT DOCUMENTS

2005/0221072 A1 10/2005 Dubrow et al.

FOREIGN PATENT DOCUMENTS

| | | | | |
|---|---|---|---|---|
| EP | 2537798 A1 * | 12/2012 | ............. | B05D 1/002 |
| WO | 2019136560 | 7/2019 | | |
| WO | WO-2019136560 A1 * | 7/2019 | ........... | A61L 31/048 |

OTHER PUBLICATIONS

Calabrese et al. "Au, Pd and maghemite nanofunctionalized hydroxyapatite scaffolds for bone regeneration", Regenerative Biomaterials, vol. 7, Issue 5, Oct. 2020, pp. 461-469. (Year: 2020).*

International Search Report and Written Opinion in corresponding International Patent Application No. PCT/IB2021/061504, mailed Mar. 29, 2022 (14 pages).

Calabrese Giovanna et al: "Abstract", Regenerative Biomaterials, vol. 7, No. 5, Oct. 1, 2020 (Oct. 1, 2020), pp. 461-469, XP055833219, ISSN: 2056-3418, DOI: 10.1093/rb/rbaa033 Retrieved from the Internet: URL:https://academic.oup.com/rb/article-pdf/7/5/461/33883720/rbaa033.pdf; Abstract; Introduction; Iron oxide nanoparticles as broad spectrum antimicrobial agent.

Vallabani N. V. Srikanth et al: "Recent advances and future prospects of iron oxide nanoparticles in biomedicine and diagnostics", 3 Biotech, vol. 8, No. 6, Jun. 1, 2018 (Jun. 1, 2018), p. 279, XP055833035, DE ISSN: 2190-572X, DOI: 10.1007/s13205-018-1286-z Retrieved from the Internet: URL:https://link.springer.com/content/pdf/10.1007/s13205-018-1286-z.pdf, Abstract; Materials and Methods.

* cited by examiner

*Primary Examiner* — Sue X Liu
*Assistant Examiner* — Casey S Hagopian
(74) *Attorney, Agent, or Firm* — Leason Ellis LLP

(57) ABSTRACT

The present invention relates to a method for the antibacterial treatment of a solid surface comprising the steps of: a) activation of said surface by means of oxygen plasma; b) deposition from the vapor phase of a silane or siloxane having at least one fluorocarburic terminal group. A method is also provided for the antibacterial treatment of a solid surface comprising the step of functionalizing said surface with nanoparticles of gamma-$Fe_2O_3$.

7 Claims, 1 Drawing Sheet

METHOD FOR THE ANTIBACTERIAL TREATMENT OF A SOLID SURFACE

CROSS-REFERENCE TO RELATED APPLICATIONS

This patent application is a U.S. National Phase Application under 35 U.S.C. § 371 of International Patent Application No. PCT/IB2021/061504, filed on Dec. 9, 2021, which claims priority from Italian patent application no. 102020000030230, filed on Dec. 9, 2020, all of which are incorporated by reference, as if expressly set forth in their respective entireties.

TECHNICAL FIELD

The present invention relates to a method for the antibacterial treatment of a solid surface.

BACKGROUND ART

With the development of the modern biomedical sector, bacterial infections of implanted medical devices have become a serious and ongoing problem. The number of infections associated with the implants of all implantable devices are around one million a year, representing a significant economic burden for society. To reduce the growing number of infections associated with implants and hospitalization costs, it is fundamental to develop materials able to prevent bacterial attachment, settlement and proliferation in these medical devices.

Among the various types of bacteria, *Staphylococcus aureus* and *Escherichia coli* are common bacteria which foul the surface of medical devices by non-specific and specific adhesion. Adhesion of the bacterial cells on the surface causes the formation of biofilm. The biofilm considerably increases survival of the bacteria and tolerance to antibiotics. Even removal of the infected implants may not fully solve the problem, because the residual bacteria can cause recurrent infections.

Three main strategies have been developed to combat the infections associated with implants: repulsion of the bacteria or a bactericidal mechanism, or a combination thereof.

The bacteria repulsion approach makes the biomaterials resistant to bacterial attack through the construction of slippery surfaces and hydrophilic antivegetative coatings.

These techniques can prevent adhesion of the bacteria) for a certain period of time without killing the bacteria which, in the end, cause fouling of the surface.

The bactericidal approach instead allows the formation of surfaces able to kill the bacteria with high effectiveness in a short time by introducing a wide range of bactericidal agents.

Some of these methods use antibiotics, silver ions or ammonium ions in the medical device. However, these methods also have some limitations such as drug resistance, and result in an increase in the biofilm.

Recently, many efforts have been made to integrate the strength of the above two antibacterial approaches in one single platform and the need is felt in the art for new methods for the antibacterial treatment of a surface, in particular, for medical devices and medical supplies.

DISCLOSURE OF INVENTION

The object of the present invention is therefore to provide a new method for the antibacterial treatment of a surface which is free from the drawbacks of the known art.

This object is reached by means of the methods described herein and recited in the appended claims.

The methods of the invention, advantageously, in addition to having antibacterial and/or bacteriostatic properties, have proved to be non-cytotoxic. They have also shown osteoinductive capacity, namely they are able to increase cell proliferation.

BRIEF DESCRIPTION OF THE DRAWINGS

For a better understanding, the present invention is now described with reference to the attached drawings, in which.

BEST MODE FOR CARRYING OUT THE INVENTION

Figure 1:
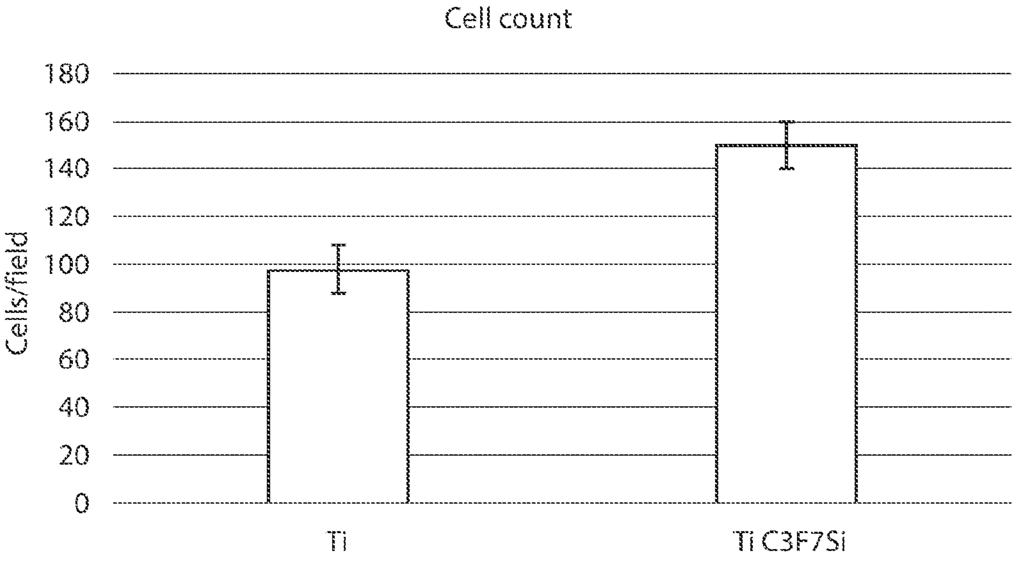
FIG. 1 shows the results of cell proliferation on a sample of titanium treated with the method according to a first embodiment of the invention.

In particular, according to a first aspect of the invention, a method is provided for the antibacterial treatment of a solid surface comprising the steps of:

a) activation of said surface by means of oxygen plasma;

b) deposition of a silane or siloxane having at least one fluorocarburic terminal group.

The surface activation step allows both removal of the organic impurities and oxidization of the surface to be functionalized with consequent increase in density of terminal hydroxyl groups (—OH) necessary for formation of the covalent bond between the surface and the silane or the siloxane deposited in the following step.

The deposition of a silane or a siloxane can be carried out by means of vapor phase deposition, liquid phase deposition or plasma deposition and allows the formation of a single layer through covalent bonds between the surface —OH groups and the silicon of the silanes or siloxanes. This deposition makes the surface highly hydrophobic with contact angle values from 80° to 140°, preventing bacterial adhesion.

The silane or the siloxane can be selected from the group consisting of hexamethyldisiloxane, trimethyl(trifluoromethyl)silane, trimethoxy(3,3,3-trifluoropropyl)silane, trichloro(1H,1H,2H,2H-perfluorooctyl)silane, 1,1,1,3,3,3-esakis(3-fluorobenzyl)disiloxane.

In one embodiment, the method according to the present invention further comprises, prior to the surface activation step, a nanostructuring step with gamma-$Fe_2O_3$ nanoparticles. Preferably the gamma-$Fe_2O_3$ nanoparticles have a dimension of 2-2000 nm.

Advantageously, nanostructuring with gamma-$Fe_2O_3$ nanoparticles promotes osteoinduction, thanks to the magnetic field generated by the nanoparticles.

The nanostructuring step can be carried out with an iron-based reagent selected from the group consisting of iron complexes with ligands belonging to the entire class of the beta-diketones such as, for example: acetylacetonate, perfluoroacetylacetonate, trifluoroacetylacetone, benzoylacetone, hexafluoroacetylacetonate, 2-furyltrifluoroacetone, 4-methyl-2-4-heptanedione, dinaphthoylmethane, 1,3-di(2-thienyl)1-3-propanedione.

According to a further aspect of the present invention, a method for the antibacterial treatment of a solid surface comprising the step of functionalizing said surface with gamma-$Fe_2O_3$ nanoparticles is also provided. Preferably this functionalization/deposition takes place by means of a photochemical method. The functionalization can take place in liquid phase or create powders photochemically and then deposit them by plasma.

The coatings obtained with the methods of the present invention furthermore have non-cytotoxic and osteoproliferative properties.

The methods of the invention allow the treatment of a surface made of a material selected from the group consisting of titanium and alloys thereof, cobalt-chrome and alloys thereof, tantalum, steel, hydroxyapatite, plastic material, natural or synthetic fiber fabric, non-woven fabric, PEEK and polyethylene.

Further characteristics of the present invention will become clear from the following description of some merely illustrative and non-limiting examples.

Example 1

Preparation of a Titanium Substrate with Hydrophobic Coating

A titanium-based sample (Ti-6Al-4V) with dimension 1×1 cm was subjected to the treatment according to the invention using trimethoxy(3,3,3-trifluoropropyl)silane as a silane reagent.

The hydrophobic coating is obtained by the formation of a monolayer having nonpolar hydrophobic terminal groups. The preparation takes place through a two-step process:

a) step of cleaning and activation of the sample surface by treatment in $O_2$ plasma for 10 minutes at 100 W.
b) silanization step in vapor phase: the sample is placed in a reactor containing 10 ml of silane reagent and kept for 4 hours at 110 °C and 0.1 Atm.

The effective functionalization of the surface was shown through contact angle measurements (table 1) and X-ray photoelectronic spectroscopy measurements (XPS) (table 2).

The XPS measurements were conducted by using a Kratos AXIS-HS instrument with Mg Kα1,2 1253.6 eV (working conditions 10 mA and 15 keV) as source. The quantitative analysis was obtained using experimental atomic sensitivity factors. Acquisition of the spectra, the processing and calculation of the quantitative chemical composition were carried out using specific software.

TABLE 1

| Substrate and treatment | Contact angle |
|---|---|
| Native Ti | 96.00° |
| Ti after treatment with step a) | 0.0° |
| Ti after treatment with step a) + b) | 106.5° |

TABLE 2

| Element | eV | Element | eV |
|---|---|---|---|
| $C_{1s}$—$F_3$ | 293.0 | $Ti_{3/2p}$ | 459.9 |
| $C_{1s}$—H2 | 286.6 | $Ti_{1/2p}$ | 465.6 |
| $C_{avv.}$ | 285 | O | 531.6 |
| Si | 102.9 | O | 533.5 |
| C—F | 689.6 | $F^-$ | 686.5 |

The SEM analysis furthermore indicates, after the silanization treatment in vapor phase, a homogeneous surface without non-uniformities or surface aggregates.

Example 2

Preparation of a Titanium Substrate Treated by Nanostructuring with Photodeposition of $\gamma$-$Fe_2O_3$ The Ti samples are positioned in a quartz photoreactor, so that the surface to be treated is exposed in the direction of the light source.

A quantity of 0.1 g of $Fe(acac)_3$ (iron tris(acetylacetonate)) is added to 500 ml of ethyl alcohol and after complete solubilization is introduced into the photoreactor.

10 ml of photosensitizer (acetone) are added and irradiated for 1.5 hours. The solution changes from red to deep yellow.

At the end of the irradiation, maintaining a constant nitrogen flow, 17 ml of NaOH 1 M are added and the solution turns darker.

The substrates are then washed with ethyl alcohol. The procedure entails at least three repetitions of the process. Lastly, the surface is dried under nitrogen flow.

Example 3

Preparation of a Titanium Substrate Functionalized with Photodeposited Nanoparticles of $\gamma$-$Fe_2O_3$ and Hydrophobic The sample obtained in example 2 was subjected to the chemical treatment as described in example 1, using trimethoxy(3,3,3-trifluoropropyl)silane as silane reagent, obtaining a surface with contact angles of approximately 100°.

The chemical-physical characterization was carried out with methods such as XPS, EDX and TEM.

The diffraction analysis of the TEM confirms by the presence of the following d-spacing values, a $\gamma$-$Fe_2O_3$ structure (2.95 Å (28%), 2.54 Å (100%), 2.09 Å (20%), 1.73 Å (10%), 1.64 Å (25%) and 1.47 Å (42%)).

The XPS analysis shows the presence of the following diagnostic peaks: C1s-F3 (293.0 eV) and C-F (689.6 eV), in addition to those typical of titanium and iron.

Example 4

Antibacterial Activity of a Surface Treated with the Method According to the Invention

Antibacterial Activity of the Sample of Example 1

Method

Different procedures for sterilization of the samples were analyzed (Ethanol 70%, UV and flowing vapor sterilization in autoclave at 121°) and two different procedures for evaluation of the antimicrobial activity by means of plate count techniques (method 1—ISO 4833-2:2013. Microbiology of the Food Chain-Horizontal Method for the Enumeration of Microorganisms—Part 2: Colony Count at 30 Degrees C by the Surface Plating Technique) and live/dead microscope acquisition (method 2) of *S. aureus* ATCC 29213, *E. coli* ATCC19138 and *P. aeruginosa* ATCC27853.

In all the tests the non-treated titanium sample was used as a negative control.

Preparation of the Inoculum a. a colony of each of the bacteria *S. aureus* ATCC 29213, *E. coli* ATTC19138 and *P. aeruginosa* ATCC27853 was inoculated in lysogeny broth (LB) medium.

b. For each bacterial strain:

the culture was incubated overnight at 37 °C;

it was then renewed, inoculating fresh culture in fresh LB medium and incubating overnight in 5 mL.

The culture was monitored in optical density until the $OD_{600}$ (Optical Density at 600 nm) was comprised between 0.4-0.8 (semi-exponential growth phase).

Preparation of the sample and evaluation of the antibacterial activity.

A sample prepared according to example 1 was inoculated with the bacteria prepared according to what was described above. The evaluation of the bacterial activity is carried out as illustrated in Acta Biomateralia 8, 2012, 904-915. doi: 10.1016/j.actbio.2011.09.031.

For each culture:

a. A culture solution of $10^7$ cells/mL was prepared by scalar dilution 1:10, considering that for all the bacteria a $OD_{600}$ of 0.3 corresponds to approximately $3*10^8$ cell/mL.

b. 60 μL of bacterial suspension ($10^7$/mL) were deposited on the upper face of the fragments (density 60 μL/cm$^2$).

c. They were left to incubate for 24 h in a humidity chamber (the test was conducted in duplicate).

d. After the incubation period, each fragment was placed in a flask containing phosphate buffered saline (PBS) and vortexed for 30 s to detach the cells adhered on the fragment.

e. The plate count was then carried out in McConkey and Cetrimide agar medium (method 1) or by live/dead coloring (method 2).

Tables 3-5 below illustrate the plate bacterial count, namely the antimicrobial activity vis-à-vis *S. aureus* (table 3), *E. coli* (table 4) and *P. aeruginosa* (table 5).

TABLE 3

| *S. Aureus* sample | Bacteria/ml (24 h) | Reduction % compared to non-treated trabecular titanium |
|---|---|---|
| Non-treated titanium | $10^7$ | 0 |
| Titanium according to example 1 | 0 | 100 |

TABLE 4

| *E. coli* sample | Bacteria/ml (24 h) | Reduction % compared to non-treated trabecular titanium |
|---|---|---|
| Non-treated titanium | $10^7$ | 0 |
| Titanium according to example 1 | $10^2$ | 99.999 |

TABLE 5

| *P. aeruginosa* sample | Bacteria/ml (24 h) | Reduction % compared to non-treated trabecular titanium |
|---|---|---|
| Non-treated titanium | $10^7$ | 0 |
| Titanium according to example 1 | $10^2$ | 99.999 |

Antibacterial Activity of the Sample of Example 2

Using the method described above, the antibacterial activity vis-à-vis the *S. aureus* of the sample obtained in example 2 was evaluated. The results are shown in table 6.

TABLE 6

| *S. Aureus* sample | Bacteria/ml (24 h) | Reduction % compared to non-treated trabecular titanium |
|---|---|---|
| Non-treated titanium | $10^7$ | 0 |
| Titanium according to example 2 | 0 | 100 |

TABLE 7

| *E. coli* sample | Bacteria/ml (24 h) | Reduction % compared to non-treated trabecular titanium |
|---|---|---|
| Non-treated titanium | $10^7$ | 0 |
| Titanium according to example 2 | 0 | 100 |

TABLE 8

| *P. aeruginosa* sample | Bacteria/ml (24 h) | Reduction % compared to non-treated trabecular titanium |
|---|---|---|
| Non-treated titanium | $10^7$ | 0 |
| Titanium according to example 2 | 0 | 100 |

Example 5

Osteo-Proliferative Activity

Osteo-Proliferative Activity of the Sample of Example 1

In order to evaluate the biocompatibility and proliferative capacity of the material analyzed we cultivated $1*10^6$ mesenchymal stem cells derived from the adipose tissue (hADSCs) on the surface of a sample of example 1 for 7 days and carried out the Trypan blue count and DAPI stain at 24 h and 7 days, to evaluate the number of cells present on each material.

For the DAPI stain, the hADSC cultivated on Ti scaffolds after 24 hours and 7 days of culture were fixed in 4% PFA, washed in PBS 1× and permeabilized in TritonX-100 at 0.3% for 10 minutes. Subsequently, the nuclei were dyed with 4', 6-diamidino-2-phenylindole (DAPI) (1:5000) in PBS 1× for 5 minutes and washed three times in PBS 1×. The digital images were acquired using a 20× magnification fluorescence microscope (Leica DMI4000B) in a random manner and 30 images (fields) were analyzed for each scaffold. The cell count from each image acquired was carried out using the Fiji image J software.

The results are shown in FIG. 1.

Osteo-Proliferative Activity of the Sample of Example 2

Figure 2:
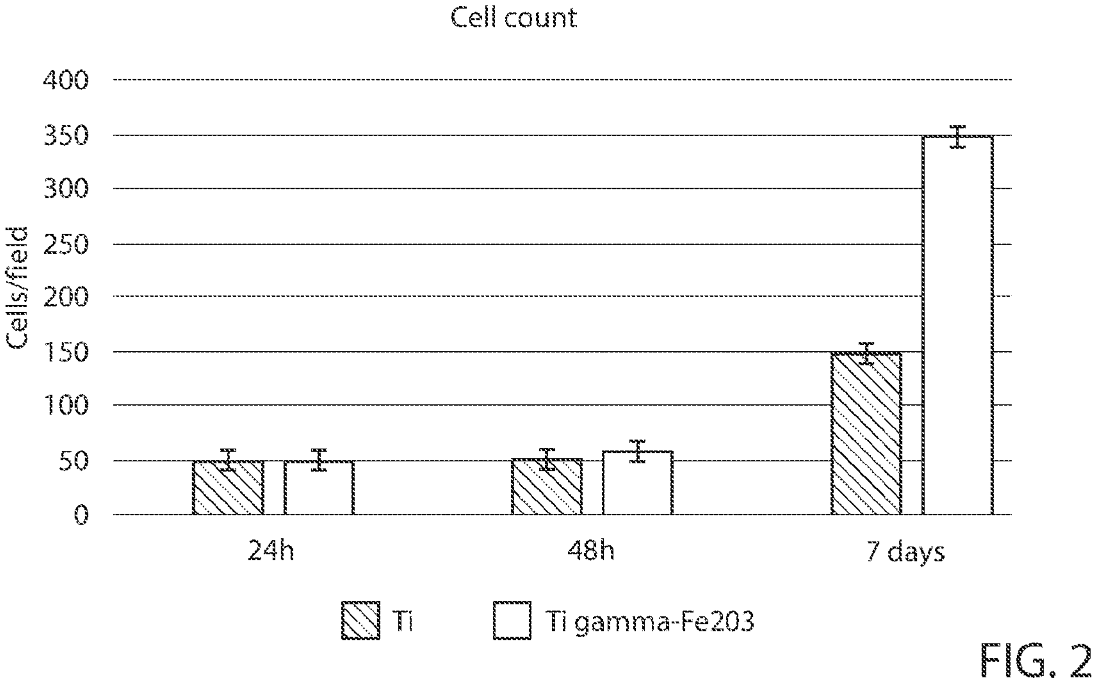
FIG. 2 shows the results of cell proliferation on a sample of titanium treated with the method according to a second embodiment of the invention.

Following the above method, the osteoproliferative activity of a treated sample as shown in example 2 was evaluated. The results are shown in FIG. 2.

The invention claimed is:

1. A method for the preparation of a solid surface with antibacterial and non-cytotoxic activity consisting in the steps of:

(a) activation of said surface by oxygen plasma;

(b) deposition of a silane or siloxane having at least one fluorocarburic terminal group; and (c) a step of functionalization of said surface with nanoparticles of gamma-Fe2O3 by liquid-phase photodeposition or plasma deposition of the particles photochemically produced in solution, before said step a).

2. The method according to claim 1, wherein said silane or said siloxane are selected from the group consisting of hexamethyldisiloxane, trimethyl(trifluoromethyl)silane, trimethoxy(3,3,3-trifluoropropyl)silane, trichloro(1H,1H, 2H,2H-perfluorooctyl)silane, and 1,1,3,3-esakis(3-fluorobenzyl)disiloxane.

3. The method according to claim 1, wherein said silane is trimethoxy(3,3,3-trifluoropropyl)silane.

4. The method according to claim 1, wherein said silane deposition phase is a vapor phase deposition, a liquid phase deposition or a plasma deposition.

5. The method according to claim 1, wherein said step of functionalization is conducted with a beta-diketone based iron complex.

6. The method according to claim 5, wherein said beta-diketone is selected in the group consisting of acetyl acetonate, perfluoroacetylacetonate, trifluoroacetylacetone, benzoylacetone, hexafluoroacetylacetonate, 2-furyltrifluoroacetone, 4-methyl-2,4-heptanedione, dinaphthoylmethane, and 1,3-di(2-thienyl)1,3-propanedione.

7. The method according to claim 1, wherein said solid surface is made of a material selected from the group consisting of titanium and its alloys, cobalt-chrome and its alloys, tantalum, steel, hydroxyapatite, plastic material, natural or synthetic fiber fabric, non-woven fabric, PEEK and polyethylene.

* * * * *